United States Patent [19]

Pevsner

[11] 4,213,461

[45] * Jul. 22, 1980

[54] MINIATURE BALLOON CATHETER

[76] Inventor: Paul H. Pevsner, 4121 King Crest Pkwy., Richmond, Va. 23221

[*] Notice: The portion of the term of this patent subsequent to Apr. 25, 1995, has been disclaimed.

[21] Appl. No.: 833,615

[22] Filed: Sep. 15, 1977

Related U.S. Application Data

[63] Continuation-in-part of Ser. No. 681,676, Apr. 29, 1976, Pat. No. 4,055,757.

[51] Int. Cl.$^2$ ............................................. A61M 25/00
[52] U.S. Cl. ..................................... 128/348; 128/656
[58] Field of Search ........... 128/2 A, 325, 348, 349 B, 128/344, 656–658

[56] References Cited

U.S. PATENT DOCUMENTS

| | | | |
|---|---|---|---|
| 3,834,394 | 9/1974 | Hunter et al. | 128/325 |
| 4,029,104 | 6/1977 | Kerber | 128/348 |
| 4,085,757 | 4/1978 | Pevsner | 128/325 |

*Primary Examiner*—Dalton L. Truluck
*Attorney, Agent, or Firm*—Griffin, Branigan and Butler

[57] ABSTRACT

A miniaturized balloon catheter assembly includes a cannula and an inflatable tubular balloon constructed of a silastic tubing detachably mounted on the cannula for performing a surgical procedure in a human vessel in response to pressure therein. In one embodiment, the balloon is detachable mounted with the detachability being responsive to pressure. For example, the balloon elastically grips the cannula and there is a small metallic C-shaped spring mounted about the balloon and cannula. In another embodiment, a valve, such as a pin-hole in the silastic material for example, is included in the balloon which opens only after the pressure within the balloon exceeds a predetermined amount.

According to a method of the invention, the cannula and the attached balloon are inserted into a small vessel and the balloon is pressurized therethrough. The balloon is partially inflated to allow fluid flow in the vessel to position the balloon at a desired location. The balloon is further inflated to fix the balloon in position against the walls of the vessel. Pressure is thereafter increased in the balloon to activate a desired procedure within the vessel. In the first embodiment the desired procedure is to withdraw the cannula from the affixed balloon as the increased pressure lubricates the connection between the balloon and the cannula. The C-spring and the silastic balloon cooperate to close off the opening into the balloon left by the retracted cannula and thereby leave the balloon in position in the vessel. In the second embodiment, the desired procedure is for the increased pressure to open the pin-hole and disperse a fluid into the vessel from the balloon. There are alternate embodiments for performing the above methods and the methods can be combined.

11 Claims, 16 Drawing Figures

MINIATURE BALLOON CATHETER

This is a continuation-in-part of application Ser. No. 681,676 filed on Apr. 29, 1976 now U.S. Pat. No. 4,085,757, issued Apr. 15, 1978.

BACKGROUND OF THE INVENTION

This invention relates broadly to the art of balloon catheters, and more particularly to the art of miniaturized balloon catheters generally for use in blood vessels and the like.

A significant publication disclosing prior art developments in the area of this invention is Serbinenko, *Balloon Catheterization and Occlusion of Major Cerebral Vessels*, Journal of Neurosurgery, Volume 41, August 1975, pages 125-145. This article describes the work of Dr. Serbinenko with miniaturized balloon catheters. Dr. Serbinenko has employed balloon catheters to occlude vessels in cardiovascular surgery as well as for other purposes, and his article is incorporated by reference here.

Dr. Serbinenko employs a latex balloon that is held onto a cannula by means of an elastic string for achieving permanent occlusion of vessels. The balloon is inserted into a vessel and allowed to move to a proper position by fluid circulation within the vessel. The balloon is then inflated by means of a solidifying filler until it is fixed against the walls of the vessel. After the solidifying filler has solidified the cannula is pulled from the balloon and the balloon is left in the vessel.

A difficulty with Dr. Serbinenko's arrangement is that the balloon sometimes comes off of the cannula prematurely because the elastic string does not tightly hold the balloon to the cannula. Still another difficulty with Dr. Serbinenko's arrangement is that the solidifying filler is somewhat difficult and awkward to work with. Thus, it is an object of this invention to provide a miniaturized balloon catheter which can be used for permanent occlusion of a vessel but which is not prematurely detached from the cannula and which can be inflated by a nonsolidifying fluid.

Dr. Serbinenko has also employed a miniaturized balloon catheter to achieve perfusion. That is, Dr. Serbinenko has made a small pin-hole in his latex balloon from which a dye or the like is discharged from the balloon into the vessel. However, in Dr. Serbinenko's arrangement, the fluid to be perfused passes through the pin-hole as soon as the fluid enters the balloon. It is sometimes desirable that the fluid not pass through the hole until the balloon has accomplished occlusion of the vessel. Thus, it is another object of this invention to provide a miniaturized balloon catheter which does not initiate perfusion of fluid until the balloon has achieved occlusion of the vessel.

It is a further object of this invention to provide a miniaturized balloon catheter, and a method for using the miniaturized balloon catheter which is efficient in operation, and relatively easy and inexpensive to manufacture.

SUMMARY

According to principles of one aspect of this invention, a miniaturized balloon catheter is inflated within a vessel until it is fixed against the walls of the vessels, and thereafter released from its attached cannula and sealed off against deflation. In this respect, the mechanism for attaching the balloon catheter to the cannula responds to increased pressure within the balloon once the balloon is fixed to release the balloon from the cannula so that the cannula can be pulled from the balloon and thereafter closes the opening in the balloon left by the extracted cannula. In one embodiment, the balloon is of a self-sealing silastic material and its diameter is approximately the same as the cannula. The balloon is fitted onto the cannula and a C-spring is mounted over the balloon and cannula to hold the balloon to the cannula. Pressure within the balloon beyond a predetermined degree opens the C-spring to allow the cannula to be removed.

Also in accordance with principles of another aspect of this invention, additional pressure within the balloon after the balloon is fixed against the walls of the vessel opens a valve in the balloon to disperse fluid from the balloon into the vessel for perfusion. This valve, in one embodiment, comprises a pin-hole in the self-sealing silastic balloon.

Additional arrangements for performing the above functions are also described herein.

To summarize, in general, the method and device of this invention deals with a miniaturized balloon catheter assembly adapted for use in diagnosis in therapy procedures in connection with small human vessels. The device includes a cannula having a small outer diameter for insertion into small human vessels. An inflatable tubular balloon is mounted on the end of the cannula that is inserted into the vessel. The cannula and balloon are adapted to be carried by fluid in the vessel to a desired location therein. The force of pressure operates at the other end of the cannula to inflate the balloon. The balloon includes elements for responding to increased pressure therein once the balloon is fixed to the walls of the vessel to initiate desired diagnostic and/or therapy procedures within the vessel at the desired location.

BRIEF DESCRIPTION OF THE DRAWINGS

The foregoing and other objects, features and advantages of the invention will be apparent from the following more particular description of preferred embodiments of the invention, as illustrated in the accompanying drawings in which reference characters refer to the same parts throughout the different views. The drawings are not necessarily to scale, emphasis instead being placed upon illustrating the principles of the invention in a clear manner.

DESCRIPTION OF PREFERRED EMBODIMENTS

Figure 1:
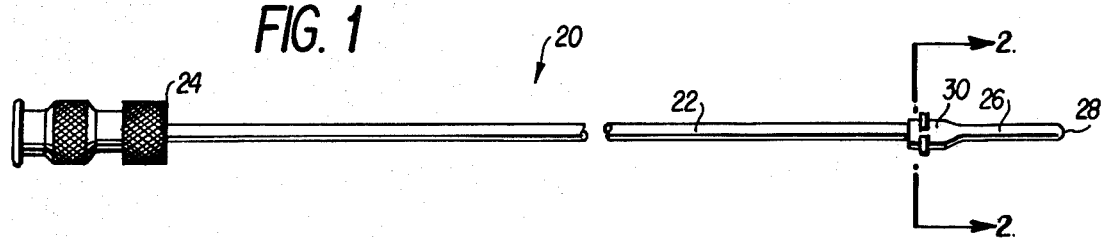
FIG. 1 is a plan view of a balloon catheter assembly of the invention.
Figure 2:
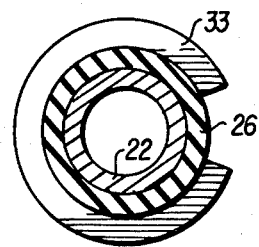
FIG. 2 is a sectional view taken on line 2—2 of FIG. 1.

FIGS. 1 and 2 show a catheter assembly 20 which includes a hollow cannula 22, open at both ends, with a connector 24 at one end which is adapted for connection to a conventional source of pressurized fluid. Mounted on the other open end of the cannula 22 is an inflatable balloon portion or inflatable tube 26 as a self-sealing material described further below. The distal end 28 of the balloon portion is closed by knotting the end. The proximal end 30 is expanded to cover and frictionally engage the adjacent end of the cannula 22. In his respect, in a preferred embodiment the interior diameters of both the balloon or tube portion 26 and the hollow cannula 22 are approximately 0.011 inch and the outer diameters thereof are 0.024 inch. Thus, the balloon or tube portion 26 contracts onto the hollow cannula 22. This brings the passageway in the cannula 22 in communication with the interior passage of the inflatable balloon portion or tube 26. As shown in FIG. 2, the inflatable tube 26 has a pin-hole 32 adjacent to the distal end 28 which is normally closed when the balloon portion 26 is in the relaxed, uninflated condition since the material of the balloon is self-sealing. This hole could also be in the distal end 28. Again this is accomplished by forming the balloon portion 26 of an elastomeric self-sealing material such as silastic tubing.

Figure 4:
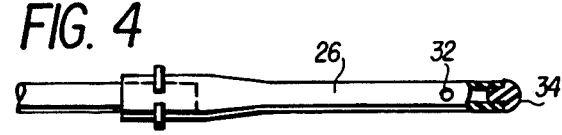
FIG. 4 is an enlarged fragmentary view thereof showing a form of inflatable balloon portion attached to the end of the cannula.

FIG. 4 shows an alternative means for forming the distal end of the balloon portion 26. In place of the knot at the end 28, a plug 34 attached by an adhesive is employed. It is also contemplated that in place of a pin-hole 32, an opening can be positioned through the knot or the plug 34. The pin-hole 32 forms a passageway for fluid to pass from the distal end of the balloon portion 26 once the pressure within the balloon portion exceeds a predetermined amount.

Materials which can be used for the components of catheter 20 are, for cannula 22, a plastic such as polyethylene or any conventional substitute therefor; and, for the expandible balloon portion 26, silastic tubing.

In addition to balloon portion 26 contracting onto the hollow cannula 22, a C-shaped spring 33 is mounted on the outside of the balloon portion to positively hold the balloon portion 26 and the hollow cannula 22 together. The C-shaped spring is constructed of a watch-spring metal and, in a preferred embodiment, this spring has a contracted internal diameter of 0.018 inches and an outside diameter of 0.020 inches. When the spring has expanded, it has an inside diameter of 0.028 inches and an outside diameter of 0.033 inches. These dimensions of the C-spring cooperate with those of the balloon portion 26 such that when the cannula 22 is not positioned within the C-spring 33 then the opening to the balloon portion 26, which the cannula 22 held open, is closed by the C-spring.

Figure 5:
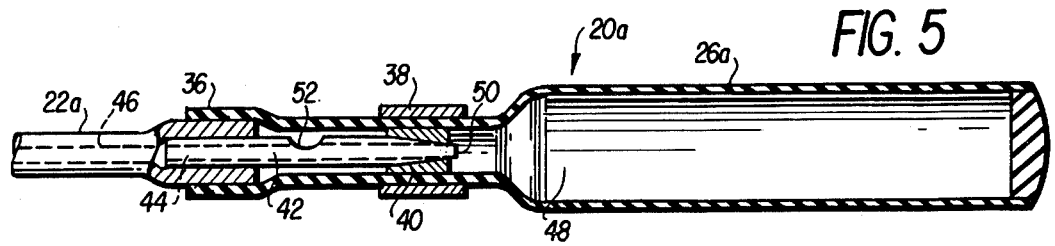
FIG. 5 is a partial sectional view of an alternate form of the balloon catheter assembly of the invention showing only the end portion of the cannula which is attached to the balloon portion.

FIG. 5 depicts an alternate device which is used as a detachable implant device for permanent vessel occlusion, for example. The materials used for cannula 22a and inflatable balloon portion 26a are the same as in the previously discussed embodiments and the difference in structure resides in the interconnection between portion 26a and cannula 22a. In place of the expanded frictional interengagement, a combination type structure is employed. In this regard, a proximal end 36 of inflatable portion 26a is expanded in the same manner and coupled with the outer surface of cannula 22a. Spaced from end 36 on portion 26a is an expandable ring 38 which is concentrically aligned with an inner plug 40. The plug is of an expandable elastomeric self-sealing material and is provided with a small pin-hole that may be formed by a wire or it may be pierced by a hollow pin 42 located within inflatable portion 26a. Pin 42 has a through passageway 44 which communicates at one end with the through passageway 46 of cannula 22a and at the other communicates with the chamber 48 in the main body portion of inflatable balloon 26a. This communication is accomplished by passing the pointed tip 50 of pin 42 through plug 40 so that its open tip is in communication from cannula 22 to the chamber 48 in balloon 26a.

An additional element of structure on pin 42 is a side opening 52 located between plug 40 and the end of cannul 22a. This side opening is utilized for activating the detachment between inflatable portion 26a and cannula 22a as will be described in detail below in connection with FIGS. 8–12. The through passageway is provided so that the fluid from the pressure source can pass into the inflatable portion and inflate balloon 26a. The FIG. 5 embodiment is perhaps cheaper to manufacture than the FIGS. 1–4 embodiments.

Figure 6:
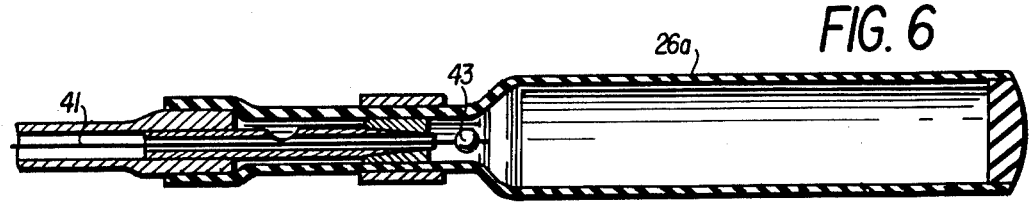
FIG. 6 is a partial sectional view of the alternate arrangement of the balloon catheter with a wire by which detachment at any balloon size may be achieved.

The embodiment of FIG. 6 is the same as the FIG. 5 embodiment with the exception of an additional wire 41 which passes through the through-passageway and terminates in a stop at the end in the form of a sphere 43. Naturally other configurations for the stop can be readily contemplated. The wire is of smaller character than the passageway so that fluid can bypass the wire and inflation can occur to the desired degree. Then the wire can be withdrawn to block the open end of tip 50 by engagement with stop 43 which closes the opening. Thereafter, further pressure will only be able to exit through side opening 52 to accomplish detachment. In this manner, no further expansion of the balloon occurs during the detachment procedure. All fluid passes through the side opening.

The embodiments of FIGS. 5 and 6 do not have the pin-hole at the distal end of portion 26a for perfusion of material contained therein. However, it is contemplated that a passageway can be provided as is present in the embodiments of FIGS. 1–4 so that the combination of detachable means and perfusion means is present in the same device.

Turning to operation of the embodiments of FIGS. 1–6, reference is made to FIGS. 8–12. It should be noted at the outset that it is possible for the device to be initially introduced into a human vessel 54 by first passing a catheter of larger diameter into the vessel and then passing the cannula 20 or 20a through the larger catheter into the vessel 54. The larger catheter can then be removed or retained in position during the remainder of the operable procedures. It is contemplated that the larger catheter through which the device can be passed can be used with all of the discussed embodiments.

Naturally the dimensions of the balloon catheter assembly are a matter of choice depending upon the particular human vessel to which it is to be applied, keeping in mind, that the device is to be used in very small human vessels. In any event, the length and lateral dimensions are determined by use. In addition to expanding the balloon portion to engage the outer surface of the end of the cannula, it is also possible to shrink the end of the balloon portion on the end of the cannula to produce the same result.

Figure 8:
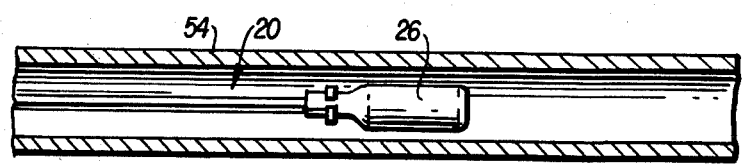
FIGS. 8–12 are sequential schematic representations of the use of the types of devices depicted in FIGS. 1–4.
Figure 9:
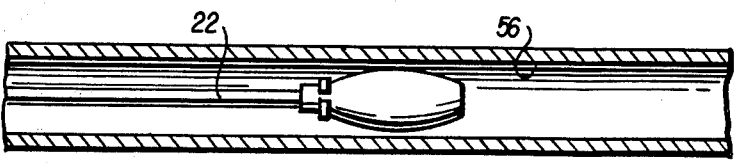
Figure 10:
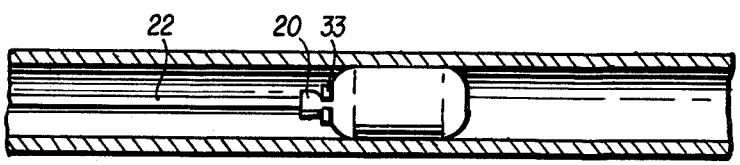

Turning to operation of cannula 20, FIG. 8 shows the cannula 20 in position in the same human vessel 54 prior to introduction of pressured fluid to expand portion 26. A first amount of pressurized fluid is then introduced as shown in FIG. 9 so as to partially expand balloon portion 26. This increases the lateral dimension of the assembly and gains the assistance of blood flowing through the vessel to push the assembly along through the vessel until it reaches the desired operable location. At that point, as shown in FIG. 10, further pressurized fluid is passed into the assembly so as to expand balloon 26 until it engages with the inner wall 56 of the vessel 54 and becomes fixed in position.

Figure 11:
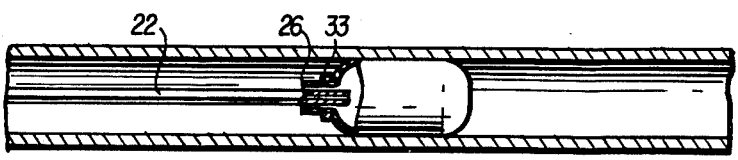
Figure 12:
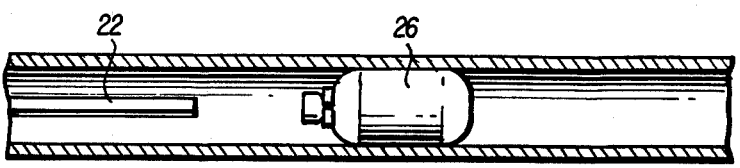

Thereafter, as shown in FIG. 11, a third stage of further pressurized fluid is passed through cannula 22. Since further expansion of balloon 26 is retarded the further fluid tries to pass between the balloon portion 26 and the cannula 22 under the C-spring 33. The passage of this fluid lubricates the connection between balloon 26 and the cannula 22 so that the cannula 22 can be relatively easily withdrawn from the balloon 26.

A similar procedure is followed for the embodiment of FIGS. 5 and 6 wherein once the balloon is fixed within the vessel so that further expansion of the balloon 26 is retarded, fluid passes through side opening 52 in the pin 42 and expands the proximal end portion of balloon 26a which is between band 38a and the proximal tip including portion 36. This expansion of portion 36 frees it from engagement with cannula 22a and permits cannula 22a and pin 42 to be withdrawn from inflatable portion 26a. There is minimal resistance between tip 50 and plug 40 due to the nature of the material of plug 40 or the prepositioned hole therein and the tapered tip 50 of the pin 42. The cannula 22a and pin 42 can thus be removed from the assembly and from the vessel 54 leaving the inflatable portion 26a in position as an implant.

Once pin 42 has been removed from plug 40 the self-sealing nature of plug 40 or the resilience of outer band 38 or both cause the plug 40 to close the opening therethrough thereby forming a valve means to seal the inflated balloon portion 26a and retain it in expanded position in proper location in the vessel.

Figure 13:
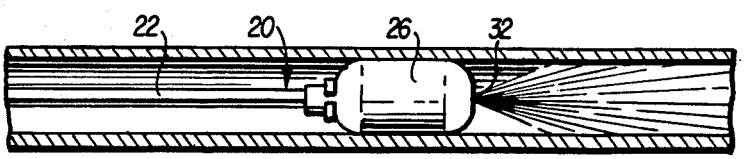
FIG. 13 is a schematic representation of the use of a balloon catheter of this invention for achieving perfusion.

Operation of the perfusion embodiment is depicted in FIG. 13. Introduction and positioning of assembly 20 is accomplished in the same manner depicted in FIGS. 8-10. Thereafter the third stage is reached at which additional fluid is introduced through cannula 22 from the fluid source and, since inflatable portion 26 is retarded from further expansion, the fluid forces a medicament or radiopaque dye, contained within the balloon portion 26, out through opening 32 in the end of body 26. Since body 26 seals the vessel at the point of its location the dye is not diluted by blood at the upstream end of the vessel and accordingly is fully effective in use at the point of perfusion.

As discussed above, the device can be a combination of the one depicted in use in FIGS. 8-12 and the one depicted in use in FIG. 13 so that perfusion can be produced and detachment achieved with perfusion continuing after the implant is made for a length of time.

Figure 3:
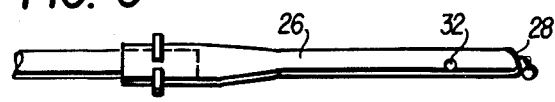
FIG. 3 is an enlarged fragmentary plan view thereof showing the inflatable balloon portion attached to the end of a cannula.
Figure 7:
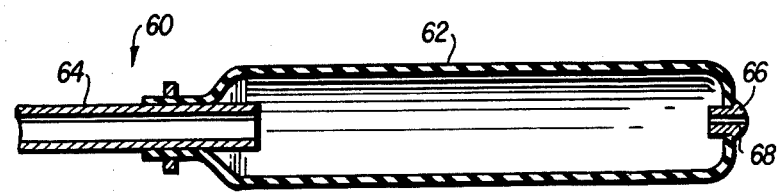
FIG. 7 is a sectional view of a further alternative form of the balloon catheter of the invention.

FIG. 7 of the drawings shows a further embodiment of the present invention wherein a balloon catheter 60 is designed for non-detachable use and, in particular, for perfusion. The balloon portion 62 is friction fit over the open end of the cannula 64 for introduction of fluid. The friction fit can be accomplished as in previous embodiments by a shrink fit between the parts or expanding the elastomeric balloon portion until it frictionally engages with the outer surface of catheter 64. The opposite end of the balloon portion has a plug 66 of self-sealing elastomeric material such as silastic with a passageway 68 therethrough normally closed in view of the nature of the material of plug 66. Sufficient introduction of fluid into balloon portion 62 willl expand the balloon portion and eventually provide sufficient pressure to cause the elastomeric plug 66 to open passageway 68 and permit perfusion of the material contained within the balloon portion to be expelled downstream. It is possible to put the opening in the balloon portion at the end as shown in FIG. 5 or in the side as shown in FIGS. 1-3 or even in the rear end portion for introduction of material from the balloon portion upstream of its location.

It is also contemplated that the introduction catheter for the embodiment shown can be of the double lumen type. That is, one lumen is directed into the balloon portion of the catheter assembly for introduction of fluid and expansion of the balloon portion; and, the other lumen is for introduction of fluid into the area of attachment between the balloon portion of the catheter. In this manner the connection portion is expanded and detachment of the components is accomplished so that the balloon portion remains as an implant. With the double lumen design, it is possible to retain a predetermined expansion level of the balloon portion since further expansion will not occur when fluid is passed only through the second lumen which opens into the area for detachment only and not into the balloon portion.

Figure 14:
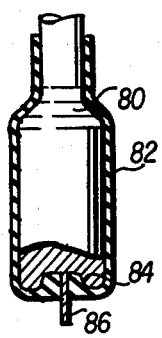
FIG. 14 is a cross-sectional view of a mandril for making a perfusion-type balloon catheter having a balloon mounted thereon positioned above a liquid silicon rubber container or vat.
Figure 14:
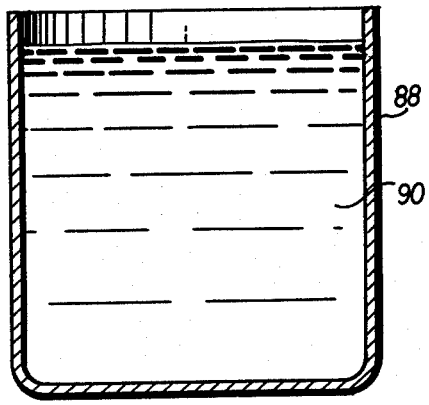
Figure 15:
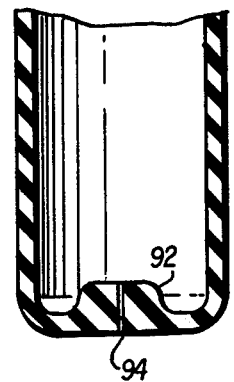
FIG. 15 is a fragmented cross-sectional side view of a perfusion-type balloon catheter constructed with the mandril of FIG. 14; and, FIG. 16 is a schematic representation of the use of a balloon catheter of this invention for achieving perfusion in another mode of operation.

FIGS. 14 and 15 depict an apparatus and method for constructing a perfusion balloon similar to the one of FIG. 7. In this respect, a steel mandril 80 on which a balloon 82 of silicon rubber, or silastic material, is molded, has an indentation 84 in the end thereof. A 0.001 inch diameter steel wire or pin 86 is part of the mandril and protrudes outwardly from the main body of the mandril at approximately the center of the indentation 84.

Figure 16:
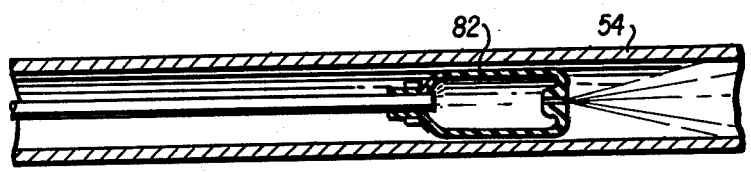

To make the balloon 82, the mandril 80 is dipped into a container or vat 88 of liquid silastic material, or silicon rubber, 90 and then pulled out. In this respect, the silicon rubber is dissolved in a solvent such as ether, para-chloro-benzene, Tolurene, etc. to put it in a liquid form. When the mandril 80 is pulled out of the liquid silastic material 90 a residue, or dispersion, or molten material is left on the mandril, with the residue at the indentation 84 being thicker than the remainder thereof. The liquid silastic material is then chemically hardened (by allowing the solvent to evaporate) on the mandril to form the balloon 82. The resilient balloon 82 is then pulled off of the mandril 80. The thicker portion of the silicon rubber forms a reinforced plug 92 having a passageway or hole 94 therethrough formed by the pin 86. The hole 94 has a diameter of approximately 0.001 inch, which is so small that, for silastic material, it is effectively closed to the passage of water-soluble fluids which are to be perfused from the balloon such as contrast media, etc. However, when the balloon is placed under pressure, the hole 94 opens at a predetermined pressure to allow fluid to pass from the balloon through the hole. In this respect, the size of the balloon at which the hole 94 opens to allow fluid passage is not only determined by the breadth and depth of the plug 92, but also by the wall thickness and length of the balloon. For example, in one embodiment the outer diameter of the balloon is approximately 0.02–0.036 inch, the inner diameter of the balloon is approximately 0.008–0.01 inch, the balloon thickness is approximately 0.005 inch, the balloon length is approximately 0.2 inch, the plug has a width of approximately 0.006–0.007 inch and a depth of approximately 0.05 inch into the balloon. In this specific embodiment the internal balloon pressure required to open the hole 94 is approximately 25 psi. The pressure in the balloon will normally not reach this level until it has expanded against the sides of a vessel as is depicted in FIG. 13. However, in some cases it is desired that the hole 94 opens and that the balloon perfuses fluid without occluding the blood vessel. This can be accomplished with the above-mentioned specific embodiment if the thickness of the balloon walls are approximately doubled, with the other dimensions remaining the same. In this case, the balloon will perfuse through the hole 94 without the balloon walls becoming wedged against the blood vessel walls as is depicted in FIG. 16.

To make the above-described balloon, the mandril is made of steel and has a width of approximately 0.008–0.01 inch. The indentation 84 has a breadth, or width, of approximately 0.006–0.007 inch, and a depth of approximately 0.05 inch to determine the size of the plug 92. The steel pin 86 has a round cross-section with a diameter of 0.001 inch. It is possible and sometimes desirable to coat the mandril including the pin, or wire, 86, with Teflon; however, it is difficult to do this and maintain the small diameter necessary for the pin. Such coating is not necessary.

It will be appreciated by those skilled in the art that the reinforced plugs desribed herein, form effective valves which are actuated by sufficient pressure within the balloons to perfuse fluid into blood vessels at predetermined and uniform pressures and balloon sizes, as was previously described.

It is noted that it is possible to cut or puncture the hole 94 in the balloon, but it is difficult to maintain the proper tolerance of hole size in this manner. Further, such cut holes are often too large. In any case, it is difficult, and possibly impossible, to construct balloon catheters in this manner which will uniformly perfuse at predetermined pressures. Such balloon catheters cannot be counted on to function uniformly.

Thus, the several aforenoted objects and advantages are most effectively attained. Although several somewhat preferred embodiments have been disclosed and described in detail herein, it should be understood that this invention is in no sense limited thereby and its scope is to be determined by that of the appended claims.

I claim:

1. A miniaturized balloon catheter assembly for use in small vessels comprising:
    an elongated tubular cannula including an attaching means at one end thereof for attaching to a source of pressurized fluid and having a small outer diameter for insertion into small vessels;
    an inflatable balloon having resilient, expandable wall means mounted on the opposite end of the cannula and in fluid communication therewith, the cannula and balloon adapted to be carried by the fluid in a vessel to desired locations therein, whereupon attachment of the cannula fluid source of pressurized fluid and introduction of amounts of pressurized fluid flow inflate the balloon;
    said balloon including an activation means responsive to further amounts of pressures to initiate a desired procedure within the small vessels, said activation means comprising a wall portion of said balloon wall means having a passageway therethrough, said passageway normally being so small that it effectively does not allow the passage of fluid from said balloon through said passageway, but said portion allowing the opening of said passageway in response to a predetermined amount of pressure within said balloon to allow passage of said fluid from said balloon into said vessels.

2. A miniaturized balloon catheter assembly as in claim 1 wherein said passageway has a round cross-section with a diameter of approximately 0.001 inch.

3. A miniaturized balloon catheter as in claim 1 wherein a reinforced portion of said balloon around said passageway forms a plug which extends inwardly into the interior of said balloon.

4. A miniaturized balloon catheter as in claim 3 wherein said passageway has a round cross-section with a diameter of approximately 0.001 inch.

5. A miniaturized balloon catheter as in claim 1 wherein said balloon having said passageway is formed by a molding process.

6. A miniaturized balloon catheter as in claim 5 wherein said balloon is formed by the process of:
    dipping a mandril into liquified resilient material of which said balloon is to be constructed, said mandril having the general shape of said balloon but including a pin protruding therefrom at the desired position of said passageway to form said passageway;
    withdrawing said mandril from said liquified material and hardening the residue of said liquified material on said mandril;
    removing said hardened material from said mandril, said hardened material forming said balloon having a passageway therethrough.

7. A miniaturized balloon catheter assembly as in claim 6 wherein said pin has a round cross-section with a diameter of approximately 0.001 inch.

8. A miniaturized balloon catheter as in claim 6 wherein said portion of said balloon is reinforced by being thicker than the remainder of said balloon.

9. A miniaturized balloon catheter as in claim 8 wherein said portion protrudes inwardly, into said balloon.

10. A miniaturized balloon catheter as in claim 1 wherein said portion of said balloon is reinforced by being thicker than the remainder of said balloon.

11. A miniaturized balloon catheter as in claim 10 wherein said portion protrudes inwardly, into said balloon.

* * * * *

UNITED STATES PATENT AND TRADEMARK OFFICE
CERTIFICATE OF CORRECTION

PATENT NO. : 4,213,461
DATED : July 22, 1980
INVENTOR(S) : Paul H. Pevsner

It is certified that error appears in the above-identified patent and that said Letters Patent are hereby corrected as shown below:

Column 1, line 17, change "1975" to --1974--; Column 4, line 30, change "cannul" to --cannula--; Column 5, line 14, change "same" to --small--; Column 6, line 19, change "willl" to --will--; Column 6, bridging lines 56 and 57, change "para-chloro-benzene" to --para-chlor-benzene--; Column 6, line 59 after "dispersion," change "or" second occurrence to --of--.

Signed and Sealed this

Twelfth Day of January 1982

[SEAL]

Attest:

Attesting Officer

GERALD J. MOSSINGHOFF

Commissioner of Patents and Trademarks